United States Patent [19]
Frankel

[11] Patent Number: 5,488,947
[45] Date of Patent: Feb. 6, 1996

[54] SLEEP AID DEVICE

[76] Inventor: Henry Frankel, 4800 W. 66th Terr., Prairie Village, Kans. 66208

[21] Appl. No.: 298,112

[22] Filed: Aug. 30, 1994

[51] Int. Cl.⁶ ..................................... A62B 19/00
[52] U.S. Cl. ............................ 128/206.22; 128/207.14; 128/201.26
[58] Field of Search ................. 128/201.26, 201.27, 128/201.28, 206.29, 207.14, 207.16, 911, 206.22

[56] References Cited

U.S. PATENT DOCUMENTS

| | | | |
|---|---|---|---|
| 1,674,336 | 1/1928 | King | 128/848 |
| 2,823,670 | 2/1962 | Page | 128/207.16 |
| 3,207,154 | 9/1965 | Rubilotta et al. | 128/206.29 |
| 3,565,071 | 2/1971 | Cobb et al. | 128/201.13 |
| 3,669,109 | 6/1972 | Cheffere et al. | 128/201.28 |
| 3,881,482 | 5/1975 | Lindholm | 128/212 |
| 4,170,230 | 10/1979 | Nelson | 128/139 |
| 4,261,354 | 4/1981 | Nelson | 128/203.23 |
| 4,262,666 | 4/1981 | Nelson | 128/203.23 |
| 4,325,365 | 4/1982 | Barbuto | 128/201.13 |
| 4,478,215 | 10/1984 | Hanlon | 128/201.13 |
| 4,676,240 | 6/1987 | Gardy | 128/207.14 |
| 4,705,033 | 11/1987 | Halfpenny | 128/201.13 |
| 4,895,143 | 1/1990 | Fisher | 128/206.29 |
| 4,941,467 | 7/1990 | Takata | 128/203.12 |
| 5,010,594 | 4/1992 | Suzuki et al. | 128/201.13 |
| 5,048,519 | 9/1991 | Kasama et al. | 128/206.29 |
| 5,092,346 | 3/1992 | Hays et al. | 128/848 |
| 5,117,816 | 6/1992 | Shapiro et al. | 128/203.24 |

Primary Examiner—Edgar S. Burr
Assistant Examiner—V. Srivastava
Attorney, Agent, or Firm—Chase & Yakimo

[57] ABSTRACT

A sleep aid device comprises a mouthpiece assembly with bit elements extending therefrom. An air assembly extends from the mouthpiece assembly and includes a humidification chamber therein. The humidification chamber comprises a plurality of cones therein for collecting moisture thereon and transfer to air streams passing therethrough. The humidified air diminishes parchment of the lips and throat. The bit elements preclude mouth closure during sleep so as to preclude the sensation of suffocation experienced upon mouth closure and also allows for user swallowing without the resulting discomfort to damaged nasal passages.

16 Claims, 2 Drawing Sheets

SLEEP AID DEVICE

BACKGROUND OF THE INVENTION

This invention relates to inhalation devices and, more particularly, to a prophylactic inhalation device for use by persons with obstructed and/or blocked nasal passages.

People with obstructed and/or blocked nasal passages may experience sleep deprivation due to such conditions. The obstructed/blocked nasal passages may be due to physical conditions or may occur after nasal operations after which the nasal passages are temporarily packed (≈five days) to control bleeding and provide support thereto. As such the patients must necessarily breathe through their mouth during such blockages.

Sleep deprivation occurs in such instances primarily due to the patient's fear of suffocation which arises upon mouth closure. Upon sensing a mouth closure the patient awakes and may find it difficult to sleep because of the fear of subsequent mouth closure. Such fear may become so pronounced that sleep may become impossible. Thus, hospitalization could result so that the distraught patient may sleep in a monitored environment.

Furthermore, upon swallowing discomfort of the patient may occur. As the act of swallowing is normally accompanied by mouth closure, air is removed from the oral and/or nasal cavities. Thus, a partial vacuum may be produced due to the blocked nasal passages. This vacuum causes discomfort of the tissues of the nasal passages particularly if the tissues are experiencing trauma due to an antecedent operation.

Finally, as the patients must breathe through their mouths the incoming air is not conditioned by the nasal passages. The throat and lips may become parched leading to more discomfort. Thus, one or more of these factors can lead to patient discomfort and sleep deprivation.

Various devices have arisen to assist patients in breathing. However, such devices have been relatively expensive, cumbersome to use and have not cost-effectively addressed the above problems.

In response thereto I have provided an inhalation device designed to be comfortably worn and maintained in place by a sleeping user. A mouthpiece assembly presents a bite plate and a downstream humidifying chamber positioned outside the wearer's mouth. The humidifying chamber encompasses a plurality of cones designed to capture moisture molecules for transfer of the moisture to an air stream passing through the chamber. The mouthpiece includes structure which displaces the dental arches so as to preclude a vacuum buildup within the oral cavity upon swallowing. Accordingly, the device addresses the major factors leading to sleep deprivation of a user experiencing nasal problems.

It is therefore a general object of this invention to provide a device to assist the inhalation process of a user having nasal obstruction and/or blockage problems.

Another object of this invention is to provide a device, as aforesaid, which precludes mouth closure of the wearer to reduce the accompanying sensation of suffocation.

Still another object of this invention is to provide a device, as aforesaid, which diminishes parched lips and diminishes parching of the throat.

A still further object of this invention is to provide a device, as aforesaid, which precludes the discomfort associated with swallowing.

Still another object of this invention is to provide a device, as aforesaid, which humidifies the inhaled and exhaled air streams.

Another object of this invention is to provide a device, as aforesaid, having a mouthpiece which is effectively retained adjacent the upper and lower dental arches of a user.

Still another object of this invention is to provide a device with mouthpiece, as aforesaid, which effectively displaces the dental arches of the user so as to inhibit production of a vacuum in the oral cavity upon swallowing.

A further object of this invention is to provide a device with mouthpiece, as aforesaid, which inhibits the entry of untreated air into the oral cavity.

Other objects and advantages of this invention will become apparent from the following description taken in connection with the accompanying drawings, wherein is set forth by way of illustration and example, embodiments of this invention.

BRIEF DESCRIPTION OF THE DRAWINGS

FIG. 7 is a plan view of the bracket of the supplemental fastening device.

DESCRIPTION OF THE PREFERRED EMBODIMENT

Figure 1A:
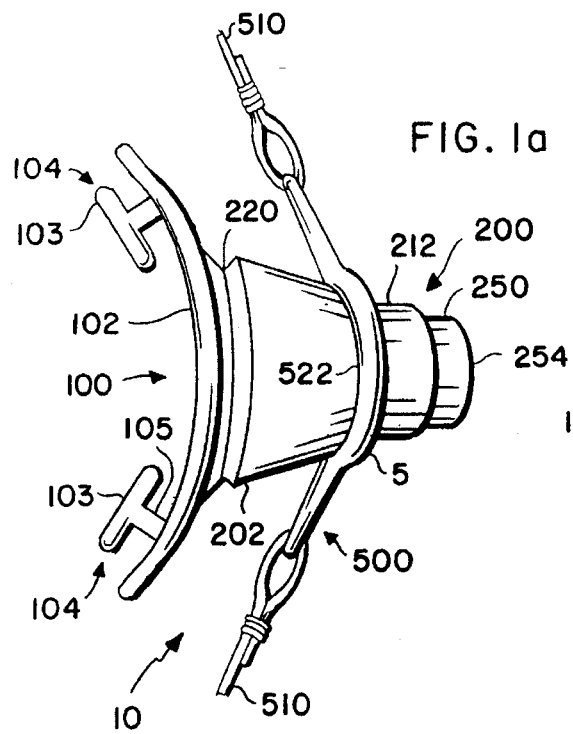
FIG. 1 is a top view of the sleep aid device.
Figure 1B:
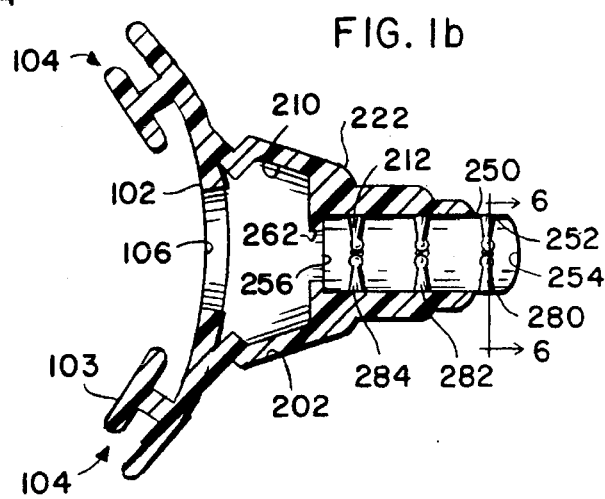
Figure 2:
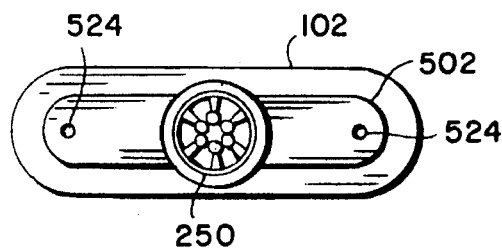
FIG. 2 is a centrally sectioned view of the device of FIG. 1 with the supplemental fastener removed.
Figure 3:
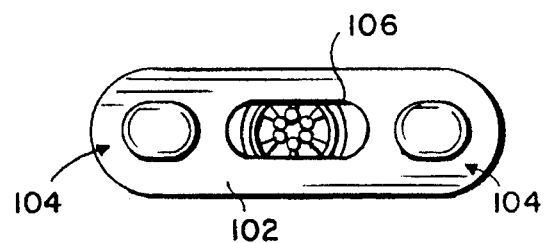
FIG. 3 is a front view of the device of FIG. 1.
Figure 4:
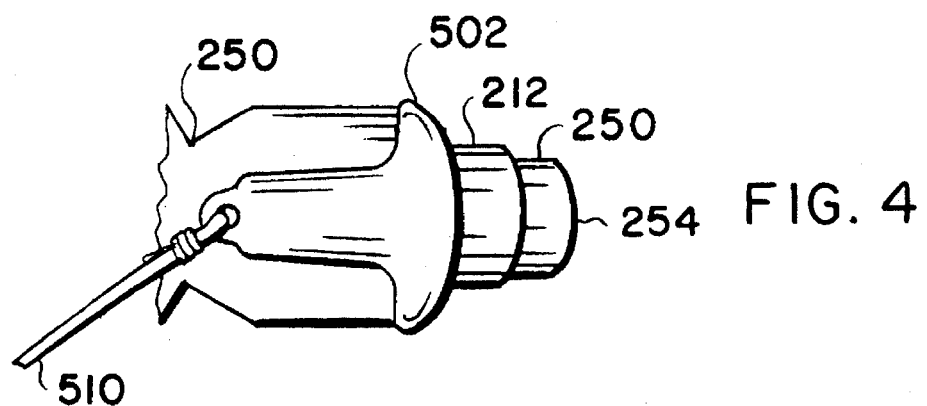
FIG. 4 is a rear view of the device of FIG. 1.
Figure 5:
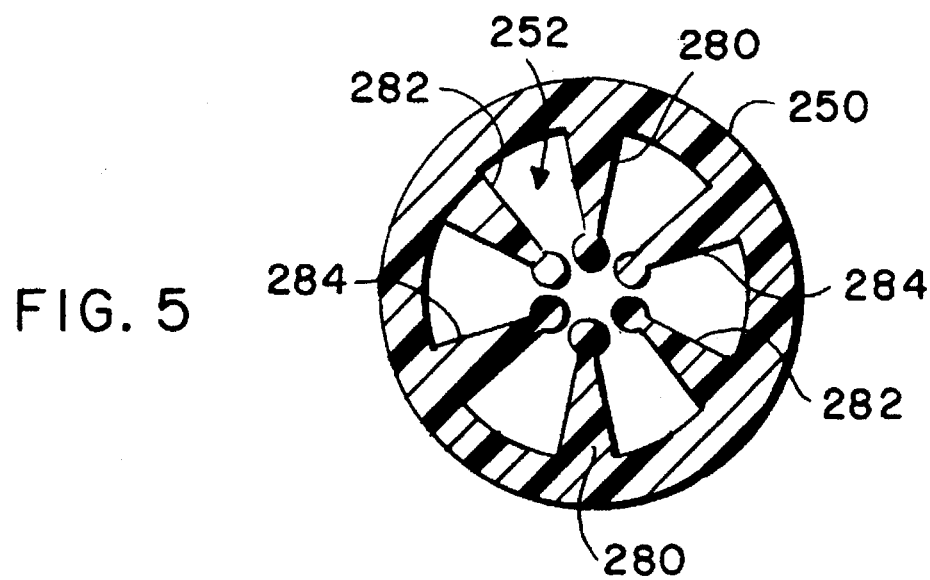
FIG. 5 is a side view of the device of FIG. 1, on a reduced scale, with the mouthpiece assembly broken therefrom to assist in illustration.
Figure 6:
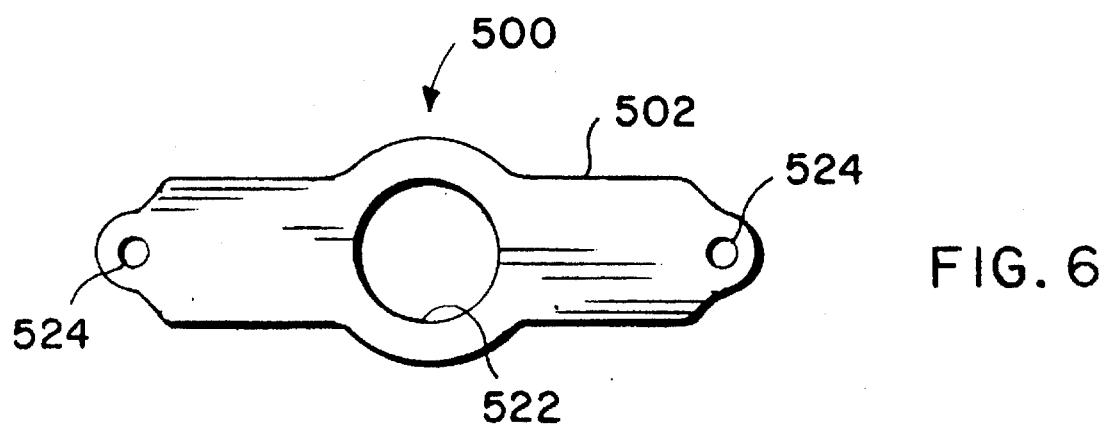
FIG. 6 is a sectional view, along line 6—6 in FIG. 2 and on an enlarged scale, of the inside of a humidifying housing to show the humidifying cones therein.

Turning more particularly to the drawings, FIG. 1 illustrates the sleep aid device 10 as generally comprising a mouthpiece assembly 100 and an air treatment assembly 200. The mouthpiece assembly 100, preferably made of a flexible material, generally comprises an arc-like plate 102 having a pair of bit elements 104 extending therefrom. An oval aperture 106 presents an air outlet 106 centrally located within the plate 102. Each bit element 104 comprises a post 105 with a lug 103 at the free end thereof. The posts 105 are adjacent the lateral ends of the plate 102 to preclude interference with incoming air being discharged from the outlet 106 and into the oral cavity.

The plate 102 configuration conforms to the shape of the front surface of the upper and lower dental arches. The plate 102 is preferably designed to bear against the front surface of the dental arches and primarily upon the upper incisors. Upon placement of the plate 102 against the dental arches the posts 105 extend between the first molars of the upper and lower dental arches. This post 105 extension positions the lugs 103 adjacent the inside surface of the dental arches behind the molars. Thus, the bit elements 104 preclude full closure of the dental arches while maintaining the plate in place. Accordingly, no significant vacuum can be produced in the mouth during swallowing which diminishes the above-described patient discomfort.

Upon placement of the mouthpiece 102 against the front surface of the dental arches the user's lips extend about the plate 102. The lips then rest in the indented annular crevice 220 extending about the primary air chamber 202. Thus, the lips form a seal around the annular crevice 220. This seal precludes passage of outside, untreated air between the lips, around plate 102 and into the oral cavity. As only treated air, as to be subsequently described, will be allowed to enter the oral cavity the above-described lip parchment and throat parchment problems are diminished.

The air treatment assembly 200 comprises a primary air housing 202 having an internal primary chamber 210 therein which surrounds the plate 102 aperture 106. Chamber 210 is in communication with a first channel 212 defined by interior and exterior apertures at the ends thereof. The housing 202 is preferably made of a relatively non-flexible material so as to allow attachment of the assembly 200 to downstream medical devices.

A humidifier housing 250 is configured to slide into the first channel or sleeve 212 of the primary air housing 202 and is held therein by a friction fit relationship therebetween. The degree of extension of the humidifier housing 250 within the channel 212 is defined by abutment with the annular shoulder 262. Accordingly, the humidifier housing 250 is releasably engageable within the channel 212.

Within the humidifier housing 250 is a second channel 252 as defined by exterior 254 and interior 252 apertures. The channel 252 contains a series of paired, opposed cones 280, 282, 284 radially extending about the channel 252 and longitudinally spaced-apart therealong. Each pair of cones is radially offset from the other, relative to the longitudinal axis of channel 252, such that air passing through channel will contact a maximum number of cones 280, 282, 284.

The interaction of the cones 280, 282, 284 with the air passing therethrough prolongs an interface of the moisture molecules with the cones as well as the interface of an air stream with these moisture-laden cones. The air stream is produced by the breathing of the wearer. Accordingly, transfer of the moisture to the air stream is enhanced. In turn moistened air is discharged from the outlet 256 of the channel 250 into the primary chamber 210, through outlet 106 and into the oral cavity.

The cones 280, 282, 284 may be fixed within the first channel 212. Thus, a humidifier housing 250 is not needed. Alternatively, the cones are positioned within the channel 252 of housing 250. The number of cones may vary. The releasable friction fit of the humidifying housing 250 within the first channel 212 allows for different humidifier housings 250 to be used having different numbers of cones therein. Alternatively, a pair of cones may extend from a ring which can be releasably fitted within the primary channel 212 of channel 252 of humidifier housing 250 channel 252.

A fastener assembly 500 is slidable over the sleeve and against shoulder 222. The fastener 500 comprises a flexible bracket 502 with aperture 522 therein to engage the annular shoulder 222. An elastic band 510 is secured at its ends to apertures 524, extended above the ears and about the head of the user. Accordingly, the fastener 500 may be used where additional assurance of maintenance of the sleep aid device 10 within the mouth of the patient is desired.

It is here noted that the outer diameter of the sleeve 212 of primary housing 200 or humidifier housing 250 may be configured so as to be easily secured to medical tubes connected to downstream medical equipment. Thus, my device 10 need not be used alone but in combination with other medical equipment.

It is to be understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. An inhalation aid device comprising:
   a mouthpiece comprising:
      a plate having a surface adapted to lie adjacent a front surface of upper and lower dental arches of a wearer;
      a poet extending from each of first and second lateral ends of said plate surface, said posts displacing the upper and lower dental arches of the wearer;
      a central aperture in said plate;
   an air treatment assembly extending from a surface of said plate and comprising:
      a housing having a first chamber at a first housing end, said first chamber in communication with said central aperture;
      a port at a free second end of said housing, said port longitudinally displaced from said first housing end and generally in line with said central aperture;
      a first channel within said housing, said first channel having a first end in communication with said first chamber and a second end presenting said port and generally in line with said central aperture and said port;
      a plurality of protuberances extending from an interior surface of said first channel, each protuberance presenting a free end adjacent an imaginary central axis longitudinally passing through said first channel, said protuberances spaced along a length of said first channel for, collecting moisture thereon from exhaled air of a wearer passing through said channel for transfer to inhaled air drawn through said port and said channel, the inhaled air discharged through said plate central aperture and between the displaced dental arches.

2. The device as claimed in claim 1 wherein said protuberances are in pairs opposite one another in said first channel, said free end of one protuberance being adjacent a free end of an opposed protuberance.

3. The device as claimed in claim 2 wherein each pair of protuberances is radially offset from an adjacent pair of protuberances about the imaginary longitudinal axis extending through said first channel.

4. The device as claimed in claim 1 further comprising a second housing, said second housing including a second channel having first and second ports at opposed first and second ends with said protuberances in said second channel, said second housing configured for insertion within said first channel with said first port in communication with said first chamber and said second port adjacent said first channel port, said second channel configured for releasable insertion with said first channel.

5. The device as claimed in claim 4 further comprising stop means in said first channel for limiting the degree of insertion of said second housing in said first channel.

6. The device as claimed in claim 4 wherein said plurality of protuberances are in pairs extending from an interior Surface of said second channel, said pairs of protuberances longitudinally displaced along said second channel with a free end of each protuberance being adjacent a free end of said other protuberance in each pair.

7. The device as claimed in claim 6 wherein each pair of said protuberances is radially offset from each other pair of protuberances about an imaginary longitudinal axis extending through said second channel.

8. The device as claimed in claim 1 further comprising a flange at an end of each post, said flange bearing against an interior surface of the dental arches to maintain said plate adjacent the front surface of the upper and lower dental arches.

9. An inhalation aid device comprising:
a mouthpiece having an aperture in communication with an oral cavity of a wearer;
an air treatment assembly comprising:
   a housing having a first chamber in communication with said mouthpiece aperture;
   a single unvalved port for air intake and discharge at a free end of said housing which freely communicates with said aperture;
   a channel extending between said first chamber and said port for providing an air flow path between said mouthpiece aperture and said port;
   a plurality of protuberances extending from a surface forming said channel and across said flow path, said protuberances presenting a free end for collecting moisture thereon from air exhaled by a wearer through said mouthpiece aperture and through said channel, the moisture available for transfer to inhaled air drawn through said port and into said channel, said air drawn through said first chamber and said mouthpiece aperture.

10. The device as claimed in claim 9 further comprising means extending from said plate for displacing the upper and lower dental arches of a wearer.

11. The device as claimed in claim 10 wherein said displacing means comprises at least one post extending from each side of said plate and between the dental arches.

12. The device as claimed in claim 11 further comprising a lug at a free end of said post for bearing against the dental arches to maintain the plate in place.

13. An inhalation aid device comprising:
a mouthpiece comprising:
   a plate having a surface adapted to lie adjacent a front surface of upper and lower dental arches of a wearer;
   means extending from first and second lateral ends of said plate surface for displacing the upper and lower dental arches of the wearer;
   a central aperture in said plate for passage of inhaled and exhaled air therethrough,
an air treatment housing extending from a surface of said plate and comprising:
   a first channel having a single unvalved port for air intake and discharge at an open distal end in communication with an outside ambient air and a proximal end in communication with said central aperture, said first channel freely communicating said port with said central aperture for presenting an air flow path between a wearer and the ambient air;
   a plurality of spaced-apart protuberances extending from a surface forming said first channel and across said air flow path whereby upon a wearer inhalation the ambient air is drawn through said air flow path for discharge through said mouthpiece aperture behind the displaced upper and lower dental arches and upon exhalation air is exhaled from a wearer in an opposed direction through said air flow path, the exhaled air depositing moisture on said protuberances.

14. The device as claimed in claim 13 wherein said protuberances comprise:
a shaft extending from an interior surface of said first channel and presenting a free end in said air flow path.

15. The device as claimed in claim 14 further comprising a head at an end of each shaft having an enlarged configuration relative to the configuration of the adjacent shaft, said head presenting a surface for collecting the moisture thereon.

16. The device as claimed in claim 13 wherein each protuberance is offset from an adjacent protuberance relative to an imaginary central longitudinal axis extending through said first channel.

* * * * *

UNITED STATES PATENT AND TRADEMARK OFFICE
CERTIFICATE OF CORRECTION

PATENT NO. : 5,488,947
DATED : February 6, 1996
INVENTOR(S) : HENRY FRANKEL

It is certified that error appears in the above-indentified patent and that said Letters Patent is hereby corrected as shown below:

Column 4, line 13, delete "poet" and substitute --post--.

Column 4, line 62, delete "Surface" and substitute --surface--.

Signed and Sealed this

Sixteenth Day of April, 1996

BRUCE LEHMAN

Attest:

Attesting Officer     Commissioner of Patents and Trademarks